United States Patent [19]
Perozzi et al.

[11] Patent Number: 5,208,382
[45] Date of Patent: May 4, 1993

[54] REDUCING COPPER CORROSIVENESS OF ORGANIC SULFIDES

[75] Inventors: Edmund F. Perozzi, Crestwood, Mo.; John F. Sieberth, Baton Rouge, La.

[73] Assignee: Ethyl Petroleum Additives, Inc., St. Louis, Mo.

[21] Appl. No.: 827,437

[22] Filed: Jan. 29, 1992

[51] Int. Cl.$^5$ .................. C07C 321/14; C07C 323/12
[52] U.S. Cl. ........................ 568/22; 568/21; 208/226; 208/230; 208/231
[58] Field of Search ............... 568/21, 22, 24; 208/226, 230, 231, 288

[56] References Cited

U.S. PATENT DOCUMENTS 4,827,040  5/1989  Labat et al. .................. 568/21

Primary Examiner—Marianne M. Cintins
Assistant Examiner—Margaret J. Page
Attorney, Agent, or Firm—John F. Sieberth

[57] ABSTRACT

The copper corrosiveness of organic sulfides is reduced by treating them with an alkali metal-containing or alkaline earth metal-containing substance capable of dissolving elemental sulfur (e.g., sodium hydroxide, sodium sulfide, etc.). The process is conducted in the presence of a phase transfer catalyst in an aqueous liquid reaction medium. Experiments have shown that it is possible by use of this process to reduce the copper corrosiveness to a level below that exhibited by a product formed by treating the same initial organic sulfide in the same way but in the absence of a phase transfer catalyst.

24 Claims, No Drawings

REDUCING COPPER CORROSIVENESS OF ORGANIC SULFIDES

TECHNICAL FIELD

This invention relates to reducing the copper corrosiveness of sulfur extreme pressure or antiwear agents, such as dihydrocarbyl polysulfides and sulfurized olefins.

BACKGROUND

Japan Kokai 59-10559 describes a process wherein dialkyl polysulfide is treated with an aqueous solution of sodium sulfide at 30°-80° C. for 1-5 hours. The treated product is indicated to have reduced copper corrosiveness, and the applicants in that laid open application express their belief that the reduction in copper corrosiveness is due to a chemical reaction whereby dialkyl tetrasulfide and dialkyl pentasulfide are converted into a less corrosive dialkyl trisulfide.

U.S. Pat. No. 4,827,040 describes a process wherein dialkyl polysulfides are treated with a variety of substances capable of dissolving elemental sulfur, such as alkali metal, alkaline earth and ammoniacal bases, hydrosulfides, alkali metal sulfites, caustic soda, caustic potash, lime, sulfides of sodium, potassium, calcium or ammonium, etc. The treatments when using such inorganic treating agents are conducted in aqueous solutions, and in the process the dialkyl polysulfides are transformed into dialkyl polysulfides having a reduced sulfur content. The most desired product of this process, according to the patentees, is dimethyl disulfide because of its usefulness as a solvent for sulfur in cleaning natural gas conduits.

THE INVENTION

This invention involves, inter alia, the discovery that it is possible to reduce the copper corrosiveness of dialkyl polysulfide to even lower levels than achieved by use of the aqueous solutions of Na₂S referred to in Japan Kokai 59-10559. Moreover this invention involves the further discovery that substances capable of dissolving elemental sulfur—i.e., alkali metal-containing and alkaline earth metal-containing substances of the type referred to in U.S. Pat. No. 4,827,040—can be used to reduce the copper corrosiveness of dialkyl polysulfides and that by modifying the treatment system, even lower levels of copper corrosiveness can be achieved. And additionally, the copper corrosiveness of dihydrocarbyl polysulfides other than dialkyl polysulfides can be effectively reduced by the practice of this invention.

In accordance with one of its embodiments, this invention provides a process of reducing the copper corrosiveness of dihydrocarbyl polysulfide that is corrosive toward copper which comprises treating such dihydrocarbyl polysulfide with a alkali metal-containing or alkaline earth metal-containing substance capable of dissolving elemental sulfur, such treatment being conducted in the presence of a phase transfer catalyst in an aqueous reaction medium.

With reference to prior processes such as are described in Japan Kokai 59-10559 and U.S. Pat. No. 4,827,040, this invention provides in a process of treating dialkyl polysulfide with an alkaline inorganic substance capable of dissolving elemental sulfur, the improvement which comprises conducting such treatment in the presence of a phase transfer catalyst in an aqueous liquid reaction medium, such that the resultant dialkyl polysulfide exhibits reduced copper corrosiveness. Indeed, as will be seen in the examples hereinafter, it is possible by use of this process to reduce the copper corrosiveness to a level below that exhibited by a product formed by treating the same initial dialkyl polysulfide in the same way but in the absence of a phase transfer catalyst.

Still another embodiment of this invention is a dihydrocarbyl polysulfide (most preferably dialkyl polysulfide) formed by a treatment process of this invention, such product being characterized by exhibiting less copper corrosiveness than a product formed from the same initial dihydrocarbyl polysulfide using the same treatment process but in the absence of the phase transfer catalyst.

These and other embodiments, features and advantages of this invention will be still further apparent from the ensuing description and appended claims.

This invention is deemed applicable to any dihydrocarbyl polysulfide having the adverse property of exhibiting excessive corrosiveness towards copper. A convenient test procedure for use in measuring copper corrosiveness is as follows: A copper coupon approximately 70×15 mm and about 1.25 mm in thickness is cleaned by use of steel wool (0000 grade), washed with heptane, and then with acetone, dried, and weighed to the nearest 0.1 mg. The cleaned coupon is placed in a test tube and covered completely with the composition to be tested, and the system is heated to 121° C, by means of an oil bath maintained at this temperature. After holding the system at 121° C. for three hours, the copper coupon is removed from the test tube, rinsed with heptane and then with acetone. The dried coupon is then rubbed with a paper towel moistened with acetone to remove any surface flakes formed by copper corrosion. The coupon is then air-dried and weighed to the nearest 0.1 mg. The difference in weight as between the initial copper coupon and the coupon after the test represents the extent to which the copper was corroded under the test conditions. Therefore the smaller the weight difference, the less the copper corrosion.

This invention is thus applicable, for example, to individual dihydrocarbyl polysulfides and mixtures of two or more dihydrocarbyl polysulfides wherein in either case at least a portion of polysulfide moiety contains at least four sulfur atoms and wherein the hydrocarbyl groups are alkyl, alkenyl, cycloalkyl, cycloalkylalkyl, aryl, aralkyl, cycloalkenyl, or the like. Such hydrocarbyl groups each can contain any number of carbon atoms, e.g., 100 or more, preferably 50 or less, most preferably up to about 18 carbon atoms, so long as the compound or mixture of compounds exhibits corrosiveness toward copper as seen for example in the above copper corrosion test. Especially preferred dihydrocarbyl polysulfides are dialkyl polysulfides containing 3 to about 18 carbon atoms in each alkyl group, most especially where the polysulfide product being treated pursuant to this invention includes at least dialkyl tetrasulfide and/or dialkyl pentasulfide.

The hydrocarbyl groups of the polysulfides used in the process can be substituted by innocuous substituents, i.e., substituents that do not interfere with or prevent the reduction in copper corrosiveness made possible by the practice of this invention. For example, the hydrocarbyl substituents of the dihydrocarbyl polysulfides may include ether oxygen atoms, thioether sulfur atoms, nitrogen atoms, etc. Thus the polysulfides used in the process of this invention include alkoxyalkyl and (polyalkoxy)alkyl-substituted polysulfides, alkylthioalkyl-substituted polysulfides, aryloxyalkyl polysulfides, dialkylaminoalkyl polysulfides, diarylaminoalkyl polysulfides, and in general, any polysulfide of the formula $R-S_n-R'$ wherein the average value of n is above 3, (preferably 3.5 or above). Thus, the average value for n may vary considerably, but usually is in the range of about 3.5 to about 12 or more. In this formula, each of R and R' is independently, any organic group (cyclic or non-cyclic) containing carbon and hydrogen, and optionally one or more oxygen, sulfur, nitrogen, and/or halogen atoms, all with the proviso that each organic group is bonded to the polysulfide moiety by a carbon-sulfur bond and the compound is corrosive toward copper and is amenable to treatment pursuant to this invention.

While this invention is discussed with reference to treatment of dihydrocarbyl polysulfides, it is contemplated that similar results can be achieved by applying the process of this invention to other sulfur-containing substances commonly employed as lubricant additives because of their extreme pressure or antiwear properties, with the proviso that such substances exhibit enough corrosiveness toward copper as seen for example in the above copper corrosion test as to warrant a treatment to effect a reduction in such corrosiveness. Substances exhibiting such corrosiveness may be found in such classes of materials as sulfurized olefins, sulfurized oils, and sulfurized fatty acid esters. The sulfurized olefins include products made by sulfurizing an olefin of up to about 6 carbon atoms (for example isobutylene) or a low molecular weight polyolefin derived therefrom such as diisobutylene with sulfur, sulfur monochloride, sulfur dichloride, hydrogen sulfide or combinations thereof. Sulfurized oils include sulfurized natural and synthetic oils such as mineral oils and lard oil. The sulfurized fatty acid esters are formed from a variety of fats and oils such as tall oil, linseed oil, olive oil, castor oil, peanut oil, rapeseed oil, fish oil, and the like.

The alkali metal-containing substance or alkaline earth metal-containing substance used in the process of this invention is any such compound or mixture of such compounds that is capable of dissolving elemental sulfur. Such compounds, many of which are referred to in U.S. Pat. No. 4,827,040, include alkali metal oxides, alkali metal hydroxides, alkali metal hydrosulfides, alkali metal mercaptides, and the corresponding alkaline earth metal compounds. Mixtures of two or more such alkali metal-containing compounds or of two or more such alkaline earth metal-containing compounds or of one or more such alkali metal-containing compound(s) with one or more such alkaline earth metal-containing compound(s) can be used. A few examples of such compounds are LiOH, NaOH, KOH, $Na_2O$, CsOH, MgO, CaO, $Mg(OH)_2$, $Sr(OH)_2$, BaO, $Ba(OH)_2$, NaSH, $NaSCH_3$, $NaSC_2H_5$, $NaSC_6H_5$, KSH, $Na_2SO_3$, $K_2SO_3$, $Na_2S$, $K_2S$, and the like. As is well known, the foregoing oxides are converted into hydroxides in the presence of water and thus when using such oxides the reaction medium in which the treatment occurs will contain hydroxide ions formed by the interaction of the oxide with water. Use of sodium oxide, potassium oxide, sodium hydroxide or potassium hydroxide, or any combination of two or more of these constitutes a preferred embodiment of this invention. Another preferred embodiment involves the use of sodium sulfide or potassium sulfide or a mixture of the two as the treating agent.

The amount of treating agent used in the process can be widely varied. All that is required is to use a sufficient amount of the treating agent to cause the resultant treated organic sulfur-containing material to have reduced copper corrosiveness as compared to the same initial material not subjected to the treatment process of this invention. The optimum quantities can thus be readily determined in any given situation by the simple expedient of performing a few tests. In most cases, the treatment process will involve use of at least about 15 parts by weight of the treating agent per 100 parts by weight of the initial dihydrocarbyl polysulfide compound being treated. Amounts of treating agent in the range of about 25 to about 300 parts by weight per 100 parts by weight of dihydrocarbyl polysulfide compound being treated are typical. However, departures from these ranges are permissible whenever deemed appropriate or desirable, and are thus within the ambit of this invention.

As noted above, the process of this invention is conducted in an aqueous liquid reaction medium in the presence of a phase transfer catalyst. It is contemplated that any of a wide variety of phase transfer catalysts may be used, including, but not limited to, crown ethers, cryptates, polyalkylene glycols, quaternary ammonium compounds, quaternary phosphonium compounds, etc. Such catalysts as 15-crown-5 and 18-crown-6 and their respective derivatives may be chosen. Preferred are the quaternary ammonium and phosphonium compounds, for example, those containing a tetrahydrocarbylammonium or -phosphonium cation, wherein the hydrocarbyl groups can be the same or different and may be alkyl, cycloalkyl, cycloalkylalkyl, aryl, aralkyl, and the like. Hydrocarbyl groups may be substituted with other atoms which do not inhibit, or which may enhance, the catalytic activity of the substance, for example, ether oxygen or halogen. The quaternary nitrogen may exist as part of a heterocyclic ring, for example, as in alkylpyridinium ion. The cation of the quaternary compound may contain up to any number of carbon atoms, for example up to about 50, but from about 4 to about 32 carbon atoms are preferred. Nonlimiting examples of cations are tetraethylammonium, tetra-n-propylammonium, tetra-n-butylammonium, tetra-n-butylphosphonium, benzyltriethylammonium, methyltrioctylammonium, tributylhexadecylphosphonium cations, and the like. Any suitable anion may be used, but preferred are halide, hydroxide, hydrogen sulfate. Thus, examples of quaternary phase transfer catalysts which may be used for carrying out the present invention include tetra-n-butylammonium hydroxide, tetra-n-butylammonium hydrogen sulfate, tetra-n-butylammonium bromide, tetra-n-butylammonium acetate, tetra-n-butylammonium chloride, tetra-n-butylphosphonium iodide, tetra-n-butylphosphonium chloride, tetrabutylammonium phosphate, tetrabutylphosphonium acetate, tetrapropylammonium hydroxide, tetra-n-propylammonium bromide, tetra-n-propylammonium hydrogen sulfate, tetra-n-propylammonium chloride, tetraethylammonium hydroxide, tetraethylammonium bromide, tetraethylammonium chloride, tetraethylammonium iodide, tetraethylammonium hydrogen sulfate, tetramethylammonium nitrate, tetramethylphosphonium chloride, tetramethylphosphonium bromide, tetra-n-octylammonium bromide, tributylhexadecylphosphonium bromide, triethylmethylammonium bromide, trimethyloctadecylammonium chloride, trimethyltetradecylammonium bromide, trimethylhexadecylammonium chloride, methyltrioctylammonium chloride, methyltrioctylammonium bromide, dimethyldioctadecylammonium chloride, hexadecylethyldimethylammonium bromide, hexadecyltri-n-butyl phosphonium bromide, hexadecyltrimethylammonium bromide, benzylhexadecyldimethylammonium chloride, benzyloctadecyldimethylammonium chloride, benzyltetradecyldimethylammonium chloride, benzyldodecyldimethylammonium chloride, benzyltriethylammonium chloride, dodecylbenzyltrimethylammonium chloride, dodecyldimethyl(2-phenoxyethyl)ammonium bromide, dodecyldimethyl-3,4-dichlorobenzylammonium chloride, hexadecylpyridinium chloride, hexadecyltrimethylammonium bromide, isobutyltriphenylphosphonium bromide, isopropyltriphenylphosphonium bromide, ethyltriphenylphosphonium acetate, ethyltriphenylphosphonium iodide, methoxymethyltriphenylphosphonium chloride, n-hexyltriphenylphosphonium bromide, phenyltrimethylammonium chloride, phenyltrimethylammonium bromide, phenyltrimethylammonium bromide, phenyltrimethylammonium chloride, tetraphenylphosphonium chloride, tetraphenylphosphonium bromide, and the like. Mixtures of any two or more of the above may be used. Especially preferred as a catalyst is tetrabutylammonium bromide.

Amounts of phase transfer catalyst used in the process of this invention may be varied to a considerable extent. Ordinarily from about 0.5 to about 25 weight percent, and preferably from about 1 to about 10 weight percent, based on the weight of the dihydrocarbyl polysulfide, will be used. On a laboratory scale, between approximately 5 and 10 weight percent of tetrabutylammonium bromide has been found efficacious. The relative proportions with respect to the water component may be varied widely provided the mixture provides adequate conditions of solubility and extractability for the treating agent the catalyst, the dihydrocarbyl polysulfide-material, and any product or by-product, to enable the treatment process to proceed efficiently and effectively.

Treatment temperatures generally fall predominantly in the range of about 35° to about 150° C., and preferably in the range of about 50° to about 90° C.

The practice and advantages of this invention are further illustrated by the following examples, which are not to be construed as limiting the scope of this invention.

EXAMPLE 1

Synthesis of Di-tert-Butyl Polysulfide

Oleylamine (1.3 g) was added to 416 g (13 mols) of sulfur. To this was added dropwise with stirring over 4.25 hours a total of 900 g (10 moles, 1125 mL) of tert-butyl mercaptan at 20°–30° C. It was noticed that when 325 mL of the mercaptan had been added, the rate of hydrogen sulfide evolution had slowed. An additional 1.3 g of oleylamine was added at this point. After addition of the mercaptan was complete, the temperature was raised to 40° C. for 0.5 hr. The temperature was raised to 70° C. and kept at this temperature for 1.5 hours. Some refluxing was noticed. High vacuum was applied and the temperature was raised to 100° C. for 40 minutes. Filtration removed a fine black precipitate. The clear, yellow mobile liquid product weighed 982.7 g (85.7% yield).

EXAMPLE 2

Treatment of Dialkyl Polysulfide with Sodium Hydroxide in the Presence of Tetrabutyl Ammonium Bromide To 7.43 g of tetrabutyl ammonium bromide and 66.67 g of sodium hydroxide dissolved in 600 mL of water was added 100 g of di-tert-butyl polysulfide prepared according to the method of Example 1. Heat was applied and the mixture was heated to about 80° C. for about 1 hour. The product was then allowed to stand, whereby two phases developed. The bottom aqueous phase was discarded and the organic phase was washed twice with 100 mL quantities of water. The organic phase was passed twice through filter paper to give a clear product and then subjected to rotary evaporation to remove any trace of water, thereby yielding 77.80 g of di-tert-butyl polysulfide product.

Samples of the di-tert-butyl polysulfide which was used in Example 2 were taken before and after the treatment of Example 2 and subjected to the above copper corrosion test (3 hours at 121° C.). Table I summarizes the results of these tests.

TABLE I

| Copper Corrosion Tests | | |
|---|---|---|
| Di-tert-butyl polysulfide used | Copper Weight Loss, mg | Corrosion Reduction % |
| Sample before the treatment of Example 2–untreated | 414.9 | — |
| Sample after the treatment of Ex. 2–per this invention | 88.9 | 78.6 |

EXAMPLE 3 (COMPARATIVE)

Treatment of Dialkyl Polysulfide With Sodium Hydroxide in Water

To a solution composed of 66.67 g of sodium hydroxide dissolved in 600 mL of water was added 100 g of di-tert-butyl polysulfide prepared as in Example 1. The mixture was heated to 80° C. and held at this temperature for approximately 1 hour. The organic phase was recovered by means of a separatory funnel and washed with 100 mL of water. The resulting organic phase (the bottom layer) was separated and subjected to rotary evaporation to remove small amounts of residual water. A total of 98.21 g of a hazy di-tert-butyl polysulfide product was obtained. This was filtered to remove residual water, thereby yielding 93.88 g of product.

Another pair of copper corrosion tests using the above procedure (3 hours at 121° C.) gave the results summarized in Table II.

TABLE II

| Copper Corrosion Tests | | |
|---|---|---|
| Di-tert-butyl polysulfide used | Copper Weight Loss, mg | Corrosion Reduction % |
| Example 1 (untreated) | 502.6 | — |
| Example 3 (treated per prior art) | 491.2 | 2.3 |

The treated products of this invention are useful as extreme pressure additives for lubricating oils. They also exhibit antioxidant and antiwear properties in lubricants.

This invention is susceptible to considerable variation in its practice within the spirit and scope of the appended claims, the forms hereinbefore described constituting preferred embodiments thereof.

What is claimed is:

1. A process of reducing the copper corrosiveness of a hydrocarbyl polysulfide in which the average number of sulfur atoms is above 3 that is corrosive toward copper which comprises treating said dihydrocarbyl polysulfide with an alkali metal-containing or alkaline earth metal-containing substance capable of dissolving elemental sulfur, such treatment being effected in the presence of a phase transfer catalyst in an aqueous liquid reaction medium at temperatures between about 35° C. and about 150° C., whereby the treated dihydrocarbyl polysulfide is less corrosive toward copper.

2. A process as claimed in claim 1 wherein the dihydrocarbyl polysulfide subjected to said treatment comprises at least dihydrocarbyl trisulfide, dihydrocarbyl tetrasulfide, and dihydrocarbyl pentasulfide.

3. A process as claimed in claim 2 wherein the dihydrocarbyl polysulfide subjected to said treatment is dialkyl polysulfide containing at least 3 but no more than about 18 carbon atoms in each alkyl group.

4. A process as claimed in claim 1 wherein said metal-containing substance used in such treatment consists essentially of alkali metal oxide or hydroxide, or both.

5. A process as claimed in claim 4 wherein said metal-containing substance used in such treatment consists essentially of sodium oxide, sodium hydroxide, potassium oxide, or potassium hydroxide, or a mixture of any two or more of the foregoing.

6. A process as claimed in claim 4 wherein said metal-containing substance used in such treatment consists essentially of sodium hydroxide.

7. A process as claimed in claim 1 wherein said metal-containing substance used in such treatment consists essentially of alkali metal sulfide.

8. A process as claimed in claim 7 wherein said metal-containing substance used in such treatment consists essentially of sodium sulfide or potassium sulfide, or a mixture of the foregoing.

9. A process as claimed in claim 7 wherein said metal-containing substance used in such treatment consists essentially of sodium sulfide.

10. A process as claimed in claim 1 wherein said phase transfer catalyst consists essentially of a quaternary ammonium phase transfer catalyst or a mixture of any two or more quaternary ammonium phase transfer catalyst.

11. A process as claimed in claim 10 wherein said phase transfer catalyst consists essentially of a quaternary ammonium halide or hydroxide or a mixture of any two or more quaternary ammonium halides or hydroxides.

12. A process as claimed in claim 10 wherein said phase transfer catalyst comprises a cation containing from about 4 to about 32 carbon atoms.

13. A process as claimed in claim 10 wherein said phase transfer catalyst consists essentially of tetrabutylammonium bromide.

14. A process as claimed in claim 1 wherein the process is conducted at treatment temperatures in the range of about 50° to about 90° C.

15. A process as claimed in claim 1 wherein the dihydrocarbyl polysulfide subjected to such treatment consists essentially of dialkyl polysulfide which comprises at least dialkyl trisulfide, dialkyl tetrasulfide, and dialkyl pentasulfide, and wherein said metal-containing substance used in such treatment consists essentially of alkali metal oxide or hydroxide, or both.

16. A process as claimed in claim 15 wherein said metal-containing substance used in such treatment consists essentially of sodium oxide, sodium hydroxide, potassium oxide, or potassium hydroxide, or a mixture of any two or more of the foregoing.

17. A process as claimed in claim 15 wherein said metal-containing substance used in such treatment consists essentially of sodium hydroxide.

18. A process as claimed in claim 15 wherein said phase transfer catalyst consists essentially of a quaternary ammonium phase transfer catalyst or a mixture of any two or more quaternary ammonium phase transfer catalysts.

19. A process as claimed in claim 18 wherein said phase transfer catalyst consists essentially of tetrabutylammonium bromide.

20. A process as claimed in claim 1 wherein the dihydrocarbyl polysulfide subjected to such treatment is a polysulfide of the formula $R-S_n-R'$ wherein each of R and R' is, independently, a hydrocarbyl substituent which includes optionally one or more of ether oxygen atoms, thioether sulfur atoms, or nitrogen atoms; wherein each said substituent is bonded to the polysulfide moiety by a carbon-sulfur bond; and wherein the average value of n is above 3.

21. A process as claimed in claim 20 wherein the average value for n is in the range of about 3.5 to about 12.

22. A process as claimed in claim 21 wherein said substance used in such treatment consists essentially of sodium oxide, sodium hydroxide, potassium oxide, or potassium hydroxide, or a mixture of any two or more of the foregoing, and wherein the phase transfer catalyst consists essentially of a quaternary ammonium phase transfer catalyst or a mixture of any two or more quaternary ammonium phase transfer catalysts.

23. In a process of treating dialkyl polysulfide in which the average number of sulfur atoms is above 3 with an alkaline inorganic substance capable of dissolving elemental sulfur, the improvement which comprises conducting such treatment in the presence of a phase transfer catalyst in an aqueous liquid reaction medium at temperatures between about 35° C. and about 150° C., such that the resultant dialkyl polysulfide exhibits reduced copper corrosiveness.

24. The process of claim 23 wherein said alkaline inorganic substance is sodium oxide, sodium hydroxide, potassium oxide, potassium hydroxide, sodium sulfide, or potassium sulfide, or a mixture of any two or more of the foregoing, and wherein the phase transfer catalyst consists essentially of a quaternary ammonium phase transfer catalyst or a mixture of any two or more of such quaternary ammonium phase transfer catalysts.

* * * * *